US012594041B2

(12) United States Patent (10) Patent No.: US 12,594,041 B2
Kin et al. (45) Date of Patent: Apr. 7, 2026

(54) INFORMATION PROCESSING SYSTEM, INFORMATION PROCESSING METHOD, AND PROGRAM

(71) Applicant: THE UNIVERSITY OF TOKYO, Tokyo (JP)

(72) Inventors: Taichi Kin, Tokyo (JP); Toki Saito, Tokyo (JP); Tatsuya Uchida, Tokyo (JP); Katsuya Sato, Tokyo (JP); Hiroshi Oyama, Tokyo (JP); Nobuhito Saito, Tokyo (JP)

(73) Assignee: THE UNIVERSITY OF TOKYO (JP)

( * ) Notice: Subject to any disclaimer, the term of this patent is extended or adjusted under 35 U.S.C. 154(b) by 337 days.

(21) Appl. No.: 18/571,506

(22) PCT Filed: Jun. 23, 2022

(86) PCT No.: PCT/JP2022/025117
§ 371 (c)(1),
(2) Date: Dec. 18, 2023

(87) PCT Pub. No.: WO2022/270584
PCT Pub. Date: Dec. 29, 2022

(65) Prior Publication Data
US 2024/0277303 A1 Aug. 22, 2024

(30) Foreign Application Priority Data
Jun. 24, 2021 (JP) ................................ 2021-104699

(51) Int. Cl.
*A61B 6/03* (2006.01)
*G06T 7/00* (2017.01)
(Continued)

(52) U.S. Cl.
CPC .............. *A61B 6/03* (2013.01); *G06T 7/0014* (2013.01); *G06T 15/08* (2013.01); *G06T 17/10* (2013.01)

(58) Field of Classification Search
None
See application file for complete search history.

(56) References Cited

U.S. PATENT DOCUMENTS 9,373,173 B2 * 6/2016 Weistrand ............... G06T 7/149
10,255,672 B2 * 4/2019 Hiraoka ................. A61B 90/37
(Continued)

FOREIGN PATENT DOCUMENTS

JP 2019-028656 A 2/2019
JP 2019-180866 A 10/2019
(Continued)

OTHER PUBLICATIONS

International Search Report of the International Searching Authority, issued in PCT/JP2022/025117, mailed Aug. 16, 2022; ISA/JP (6 pages).

*Primary Examiner* — Marcus H Taningco
(74) *Attorney, Agent, or Firm* — Harness, Dickey & Pierce, P.L.C.

(57) ABSTRACT

An information processing system is provided. The information processing system comprises at least one processor configured to execute a program so that each following step is executed. In a reconstruction step, a first volume data is reconstructed, the first volume data indicating at least a part of the subject based on a plurality of first serial tomographic images of the subject. The first volume data includes first contour data representing an exterior of the subject and internal data including the inside of the subject. In a conversion step, the first volume data is converted to second volume data based on reference contour data other than the first contour data, the second volume data includes a second (Continued)

contour data different from the first contour data and the internal data including the inside of the body of the subject including the first contour data and the internal data including the inside of the body of the subject.

13 Claims, 12 Drawing Sheets

(51) Int. Cl.
G06T 15/08        (2011.01)
G06T 17/10        (2006.01)

(56)                    References Cited

U.S. PATENT DOCUMENTS

| | | | |
|---|---|---|---|
| 2016/0135776 A1* | 5/2016 | Chandler, Jr. | A61B 5/055 600/411 |
| 2018/0232944 A1* | 8/2018 | Barski | G06T 11/008 |
| 2019/0080459 A1* | 3/2019 | Lachaine | A61N 5/1049 |
| 2020/0118317 A1 | 4/2020 | Mysore Siddu et al. | |
| 2020/0342990 A1 | 10/2020 | Ichinose et al. | |
| 2022/0230319 A1* | 7/2022 | Andersson | G06T 7/0016 |

FOREIGN PATENT DOCUMENTS

| | | |
|---|---|---|
| JP | 2020-091770 A | 6/2020 |
| JP | 2020-525926 A | 8/2020 |
| JP | 2021-051471 A | 4/2021 |
| WO | 2019/146357 A1 | 8/2019 |

* cited by examiner

4a

4b

4c

4d

4e

4f

4g

IM1

V1

$\underline{V0}$

V1

○ LANDMARK LM

V0

○ LANDMARK LM

V2

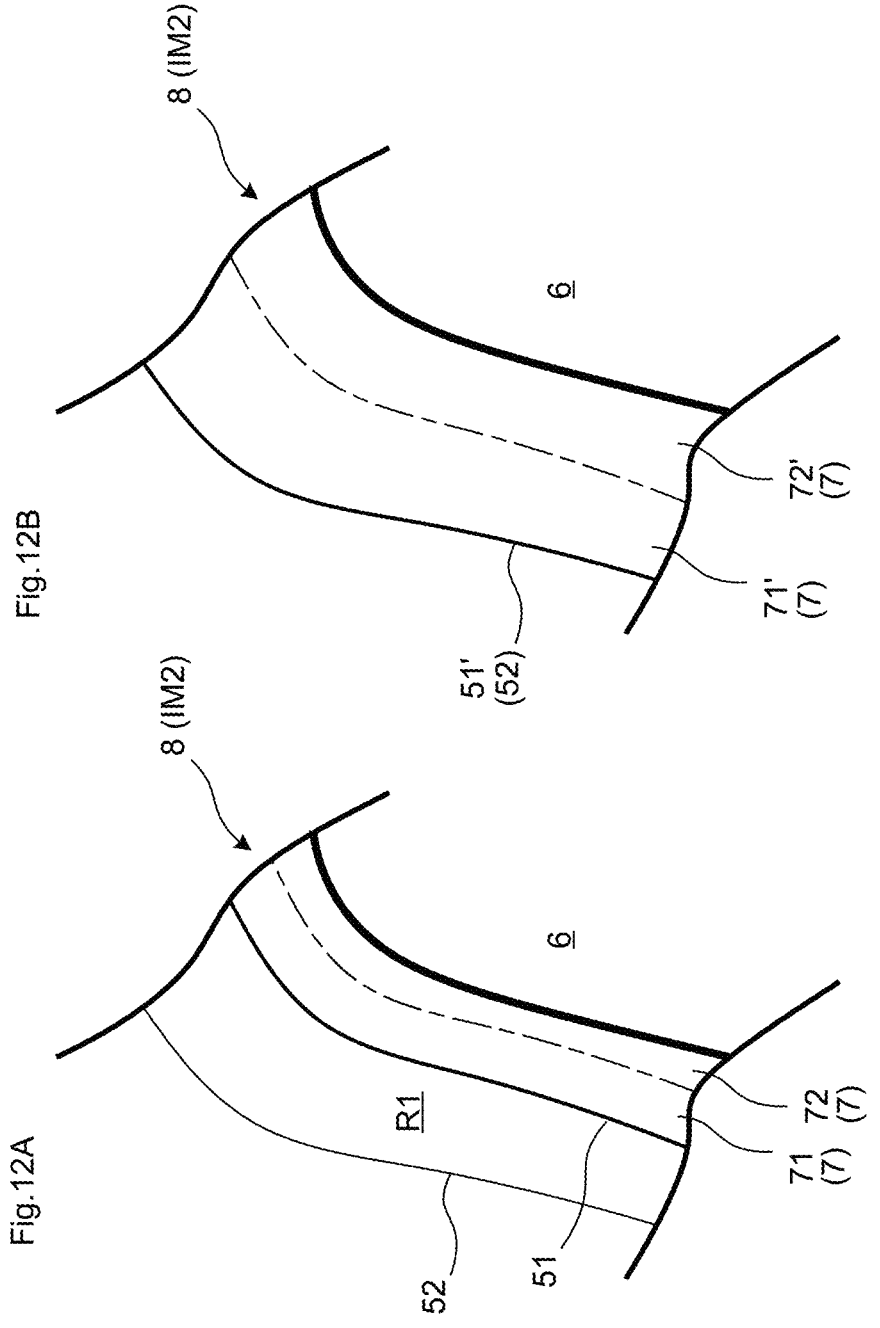

INFORMATION PROCESSING SYSTEM, INFORMATION PROCESSING METHOD, AND PROGRAM

CROSS REFERENCE TO RELATED APPLICATIONS

This application is a 371 U.S. National Phase of International Application No. PCT/JP2022/025117, filed on Jun. 23, 2022, which claims priority to Japanese Patent Application No. 2021-104699, filed Jun. 24, 2021. The entire disclosures of the above applications are incorporated herein by reference.

BACKGROUND

The present invention relates to an information processing system, information processing method and program.

RELATED ART

In recent years, medical images captured by medical imaging apparatus have been used as teacher data for machine learning (e.g., Patent Publication JPA2019-180866). In addition, such a program based on machine learning can be used by a physician to assist his/her diagnosis.

However, if, for example, the medical image is a serial tomographic image obtained by an X-ray CT scanner or similar device, it can be reconstructed to reproduce the face of the subject in a recognizable manner. For this reason, concerns have been raised about the use of such data as teacher data from the viewpoint of personal information protection.

In view of the above circumstances, the present invention provides information processing systems, etc., which can guarantee the anonymity of medical images.

SUMMARY

According to an aspect of the present invention, an information processing system is provided. The information processing system comprises at least one processor configured to execute a program so that each of the following steps is executed. In a reconstruction step, a first volume data is reconstructed, the first volume data including at least a part of the subject based on a plurality of first serial tomographic images of the subject. the first volume data includes first contour data representing an exterior of the subject and internal data including the inside of the subject. In a conversion step, the first volume data is converted to second volume data based on reference contour data other than the first contour data. the second volume data includes a second contour data different from the first contour data and the internal data including the inside of the body of the subject including the first contour data and the internal data including the inside of the body of the subject.

According to such a mode, the anonymity of medical images can be ensured.

BRIEF DESCRIPTION OF THE DRAWINGS

FIGS. 12A and 12B are schematic diagrams indicating the correction by deforming internal data 6.

DETAILED DESCRIPTION

The following drawings are used to describe the embodiments of the invention. The various features shown in the following embodiments can be combined with each other.

A program for realizing a software in the present embodiment may be provided as a non-transitory computer readable medium that can be read by a computer or may be provided for download from an external server or may be provided so that the program can be activated on an external computer to realize functions thereof on a client terminal (so-called cloud computing).

In the present embodiment, the "unit" may include, for instance, a combination of hardware resources implemented by a circuit in a broad sense and information processing of software that can be concretely realized by these hardware resources. Further, various information is executed in the present embodiment, and the information can be represented by, for instance, physical values of signal values representing voltage and current, high and low signal values as a set of binary bits consisting of 0 or 1, or quantum superposition (so-called qubits), and communication/calculation can be executed on a circuit in a broad sense.

Further, the circuit in a broad sense is a circuit realized by combining at least an appropriate number of a circuit, a circuitry, a processor, a memory, and the like. In other words, it is a circuit includes application specific integrated circuit (ASIC), programmable logic device (e.g., simple programmable logic device (SPLD), complex programmable logic device (CPLD), and field programmable gate array (FPGA)), and the like.

Embodiment

Figure 1:
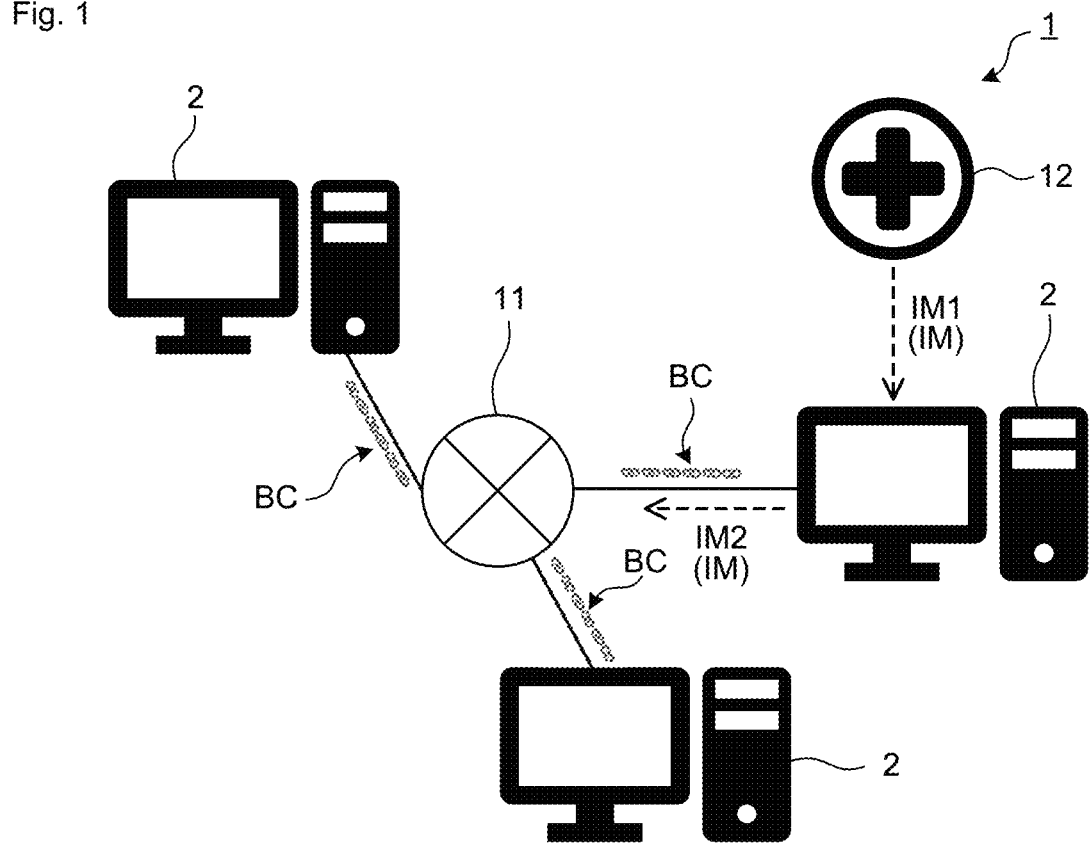
FIG. 1 is a configuration diagram representing an information processing system 1 according to one embodiment.

1. Hardware Configuration
This section describes the hardware configuration of this system.
1.1 Information Processing System 1
FIG. 1 is a configuration diagram representing an information processing system 1 according to one embodiment.

The information processing system 1 comprises at least one information processing apparatus 2, which are connected through a network 11. Here, the information processing apparatus 2 is depicted as a plurality of information processing apparatus 2. The information processing apparatus 2 are configured to enable distributed management of various types of information using blockchain BC or the like. A system exemplified in the information processing system 1 comprises one or more devices or components. Therefore, even information processing apparatus 2 alone is an example of a system.

1.2 Information Processing Apparatus 2

Figure 2:
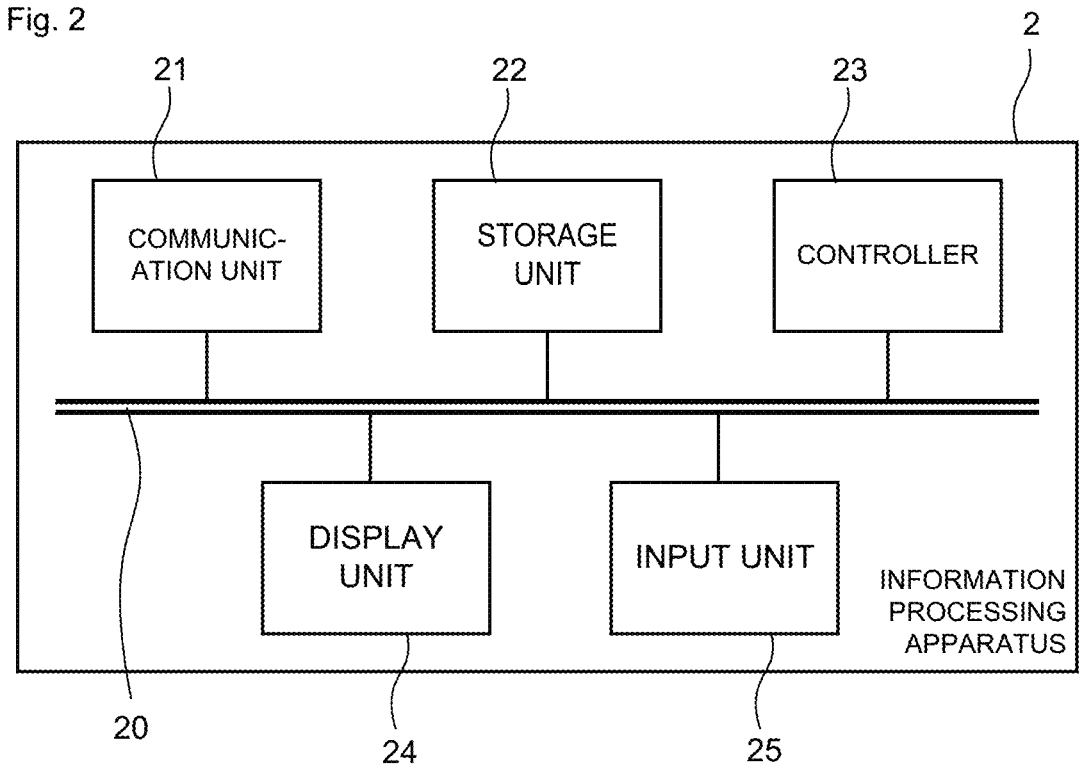
FIG. 2 is a block diagram indicating a hardware configuration of an information processing apparatus 2 according to one embodiment.

FIG. 2 is a block diagram indicating the hardware configuration of the information processing apparatus 2 according to one embodiment. The information processing apparatus 2 comprises a communication unit 21, a storage unit 22, a controller 23, a display unit 24, and an input unit 25, and the components thereof are electrically connected inside the information processing apparatus 2 via a communication bus 20. Each component will be further described.

The communication unit 31 preferably uses wired communication means such as USB, IEEE 1394, Thunderbolt, wired LAN network communication, etc., but wireless LAN network communication, mobile communication such as 3G/LTE/5G, Bluetooth (registered trademark) communication, etc. may be included as necessary. In other words, it is preferable to implement a set of these multiple communication means. This allows information and command to be exchanged between the control apparatus 3 and other communicable apparatus.

In one embodiment, the information processing apparatus 2 is configured to communicate transaction information about the blockchain BC with external devices, including other information processing apparatus 2 via the network 11 and the communication unit 21. The blockchain BC is described below in the following description of the storage unit 22.

The storage unit 22 stores various information as defined by the foregoing description. It can be implemented, for example, as a storage device such as a solid state drive (SSD) that stores various programs, etc. pertaining to the information processing apparatus 2 executed by the controller 23, or as a memory such as random access memory (RAM) that stores temporarily necessary information (arguments, sequences, etc.) pertaining to program operations. Further, combination thereof may also be used.

In particular, in one embodiment, the storage unit 22 stores a program that causes the computer to execute each step in the information processing system 1. In other words, by having such a program installed in the information processing apparatus 2, the information processing apparatus 2 includes each functional unit and is configured to execute each step as described below.

The storage unit 22 is configured to store the tokenized information in a blockchain BC, which is an example of a distributed ledger. A distributed ledger is an electronic ledger. The distributed ledger is shared by multiple nodes by a plurality of information processing apparatus 2.

In the blockchain BC, data is recorded as multiple blocks that are beaded together, and each node is implemented to share these blocks. Each information processing apparatus 2 functions as a node in the distributed ledger. It is noted that the distributed ledger initially includes the first block, the origin block, registered as the initial value. Newly generated blocks are connected to the origin block. The block contains transaction information. The transaction information in this form includes the second serial tomographic image IM2, which is described below.

The controller 23 (processor) processes and controls the overall operation related to the information processing apparatus 2. The controller 23 is, for example, an unshown central processing unit (CPU). The controller 23 reads a predetermined program stored in the storage unit 22 to realize various functions related to the information processing apparatus 2. In other words, the information processing by software stored in the storage unit 22 is specifically realized by the controller 23, which is an example of hardware. In other words, the information processing system 1 comprises the controller 23, which is equipped with each functional unit described below.

The display unit 24, for example, may be included in the housing of the information processing apparatus 2, or may be external. The display unit 24 displays a graphical user interface (GUI) screen that can be operated by the user. This should be implemented, for example, by using different display devices such as a CRT display, liquid crystal display, organic EL display, and plasma display, depending on the type of information processing apparatus 2.

Input unit 25 may be included in the housing of information processing apparatus 2 or may be external. For example, the input unit 25 may be integrated with the display unit 24 and implemented as a touch panel. With a touch panel, the user can input taps, swipes, etc. Of course, a switch button, mouse, QWERTY keyboard, etc. may be employed instead of a touch panel. In other words, the input unit 25 receives operation inputs made by the user. Said input is transferred as an instruction signal to the controller 23 via the communication bus 20, and the controller 23 can perform predetermined control and operations as necessary.

2. Functional Structure

This section describes the functional structure of the present embodiment. As mentioned above, information processing by software stored in storage unit 22 is specifically realized by controller 23, which is an example of hardware, and can be executed as each functional unit included in controller 23.

Figure 3:
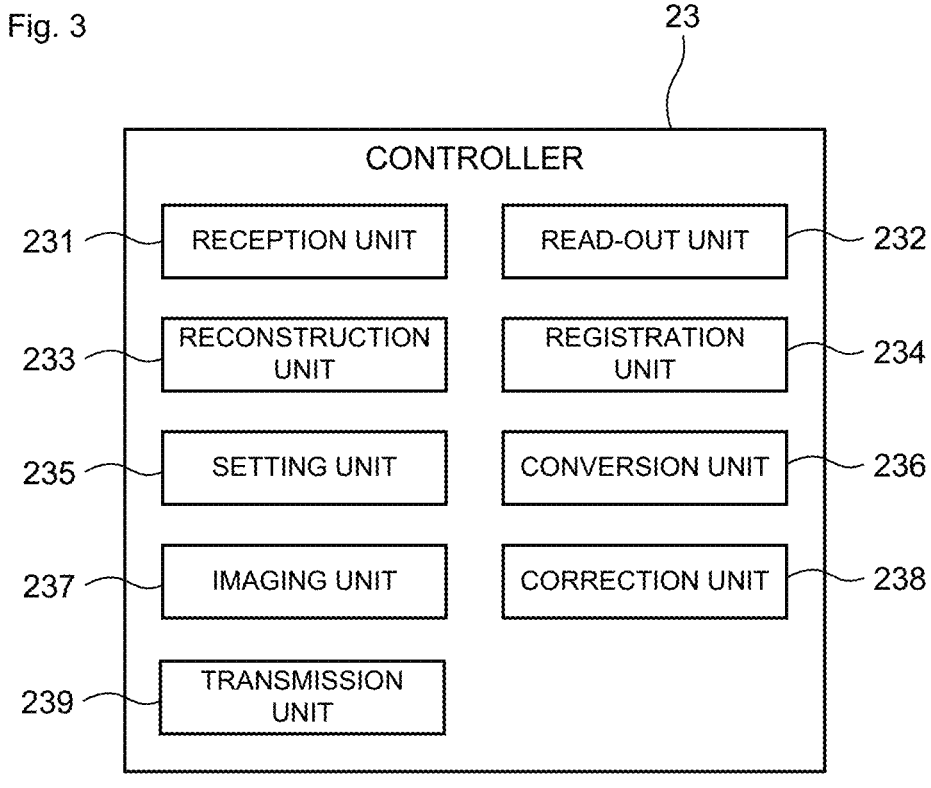
FIG. 3 is a block diagram indicating functions realized by a controller 23 etc. in the information processing apparatus 2 according to one embodiment.

FIG. 3 is a block diagram indicating the functions realized by the controller 23 etc. in the information processing apparatus 2 according to one embodiment. Specifically, the information processing apparatus 2, which is an example of the information processing system 1, is equipped with a reception unit 231, a read-out unit 232, a reconstruction unit 233, a registration unit 234, a setting unit 235, a conversion unit 236, an imaging unit 237, a correction unit 238 and a transmission unit 239.

The reception unit 231 is configured to receive various information from outside via the network 11 or through an unshown recording media. For example, the reception unit 231 may receive a first serial tomographic image IM1 of the subject provided by the hospital 12 via an unshown recording media. The first serial tomographic image IM1 received by the reception unit 231 is stored in the storage unit 22 of the information processing apparatus 2. This will be described in further detail later.

The read-out unit 232 is configured to read out various information received by the reception unit 231 or stored in the storage unit 22 in advance. For example, the read-out unit 232 may read out the first serial tomographic image IM1 stored in the storage unit 22, reference volume data V0 or reference contour data 50 etc., which are examples of reference information. This will be described in further detail later.

The reconstruction unit 233 is configured to reconstruct the volume data V by reconstructing the serial tomographic image IM. For example, the reconstruction unit 233 may reconstruct the first volume data V1 indicating at least a part of the subject based on the first serial tomographic image IM1 stored in the storage unit 22. This will be described in further detail later.

The registration unit 234 is configured to execute the registration process between the first volume data V1 and the reference volume data V0 with reference contour data 50 representing the exterior of the fictitious person. This will be described in further detail later.

The setting unit 235 is configured to set a landmark LM for the first volume data V1 and the reference contour data 50, which are registered with each other. This will be described in further detail later.

The conversion unit 236 is configured to convert the first volume data V1 to the second volume data V2 based on the reference contour data 50 as the conversion step. This will be described in more detail later.

The imaging unit 237 is configured to generate a plurality of serial tomographic images IM from the volume data V with a predetermined slice thickness. For example, the imaging unit 237 may generate a plurality of second serial tomographic images IM2 from the second volume data V2. This will be described in further detail later.

The correction unit 238 is configured to execute a correction to stretch or shrink the intermediate data 7 to fit the second contour data 52. This will be described in further detail later.

The transmission unit 239 is configured to transmit various information externally via the communication unit 21 and the network 11. For example, the transmission unit 239 may transmit at least a part of the second serial tomographic image IM2 to an external device, for example, another information processing apparatus 2. This will be described in further detail later.

3. Information Processing Method

This section describes the information processing method of the information processing system 1 described above. Hereinafter, assumed is that the case where a subject using the information processing apparatus 2 undergoes a medical image diagnosis at a hospital 12 and the first serial tomographic image IM1, the result of the diagnosis, is provided as teacher data. The device used for the medical image diagnosis is, for example, an X-ray CT scanner, a magnetic resonance imaging apparatus, or the like. For example, in the case of an X-ray CT scanner, an X-ray detector detects X-rays irradiated from an unshown X-ray tube and outputs detection data corresponding to the X-rays as electrical signals to an unshown DAS. Then, by rotating the unshown rotation frame that supports the X-ray tube and X-ray detector facing each other around the subject, detection data is collected for multiple views, i.e., for the entire circumference of the subject. Thereby, a serial tomographic image IM is obtained.

Further, the volume data V obtained by reconstructing the serial tomographic image IM includes contour data 5 representing the exterior and internal data 6 including the inside of the body. Further, the volume data V includes intermediate data 7 that indicates the region between the contour data 5 and the internal data 6. Further, when one of the serial tomographic images IM is extracted, it will likewise be referred to as the contour data 5, internal data 6, and intermediate data 7 of the serial tomographic image IM, respectively. In the present embodiment of medical imaging, the physician identifies the case by observing the internal data 6 in the serial tomographic image IM.

3.1 Overview of Information Processing

Figure 4:
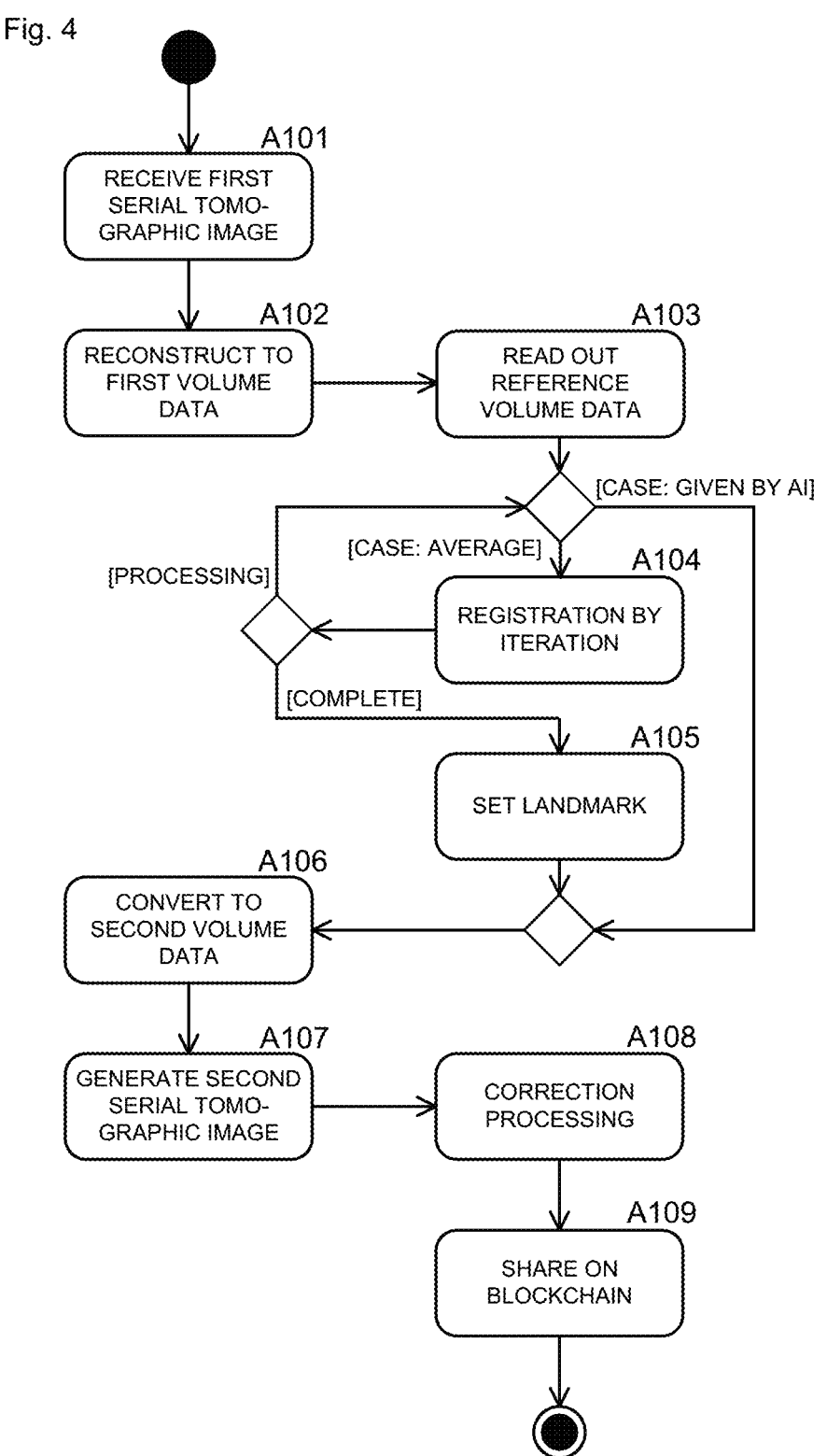
FIG. 4 is an activity diagram indicating a flow of information processing executed by the information processing apparatus 2 according to the first embodiment.

FIG. 4 is an activity diagram indicating a flow of information processing executed by the information processing apparatus 2 according to the first embodiment. First, the flow of the information processing is outlined along each activity in FIG. 4.

At the beginning, the reception unit 231 receives the first serial tomographic image IM1 as a reception step. Specifically, the subject, a user of the information processing apparatus 2, allows the information processing apparatus 2 thereof to read the first serial tomographic image IM1 recorded on an unshown recording media provided by the hospital 12, thereby storing the first serial tomographic image IM1 in the storage unit 22 (Activity A101).

Subsequently, the reconstruction unit 233 reconstructs the first volume data V1 indicating at least a part of the subject based on the plurality of first serial tomographic images IM1 of the subject as a reconstruction step. Specifically, such reconstruction step is executed by the controller 23 reading a program with a reconstruction function stored in the storage unit 22 (Activity A102).

The read-out unit 232 then reads out the reference volume data V0 which is an example of reference information stored in advance in the storage unit 22, and writes the same to the temporary storage area of the storage unit 22 (Activity A103). If the reference contour data 50 contained in the reference volume data V0 being read out is calculated by the average of a plurality of person images, the processing proceeds to Activities A104 and A105. On the other hand, if the reference contour data 50 is generated based on a learned model such as GAN, for example, the processing described in Activities A104 and A105 can be omitted. Activities A104 and A105 are explained below.

The registration unit 234 executes the registration process between the first volume data V1 and the reference volume data V0 with reference contour data 50 as a registration step. Specifically, it is preferred that the controller 23 reads out the program with the registration function stored in the storage unit 22, the iteration calculation (repetition of activity A104) is executed, and the positional relationship between the reference volume data V0 and the first volume data V1 for which the evaluation function obtains extreme values is automatically calculated.

Subsequently, the setting unit 235 sets landmarks LM for the first volume data V1 and reference volume data V0, which are aligned with each other as a setting step. The landmark LM is a tracking point that can be a feature point, which is further described below. Specifically, such setting step is executed by the controller 23 reading a program with a landmark setting function stored in the storage unit 22 (Activity A105).

Subsequently, as the conversion step, the conversion unit 236 converts the first volume data V1 into the second volume data V2 with the second contour data 52 based on the landmark LM. Here, the internal data 6 is not transformed before and after the conversion, only the contour data is transformed from the first contour data 51 to the second contour data 52. Specifically, such a conversion step is executed by the controller 23 reading a program with a conversion function stored in the storage unit 22 (Activity A106).

Subsequently, the imaging unit 237 generates a plurality of second serial tomographic images IM2 from the second volume data V2 as an imaging step. Specifically, such imaging step is executed by the controller 23 reading a program with an imaging function stored in the storage unit 22 (Activity A107).

Subsequently, The correction unit 238 corrects the second serial tomographic image IM2 by executing a correction to stretch or shrink the intermediate data 7 to fit the second contour data 52 as a correction step. Specifically, such correction step is executed by the controller 23 reading a program with a correction function stored in the storage unit 22 (Activity A108).

Finally, the transmission unit 239 transmits at least a part of the second serial tomographic image IM2 to an external device as a transmission step. Such transmission may be determined by an input of the subject operating the information processing apparatus 2 with respect to the input unit 25. More specifically, the second serial tomographic image IM2 corrected in Activity A108 is recorded in a block of the blockchain BC and shared (here, distributed ledger management) among a plurality of information processing apparatus 2 via the network 11 (Activity A109). According to such a mode, the subject can, of his/her own free will, provide his/her own medical image, here the second serial tomographic image IM2, as teacher data while ensuring anonymity.

In summary, the information processing method described above comprises the following steps. In the reconstruction step, a first volume data V1 indicating at least a part of the subject is reconstructed based on a plurality of first serial tomographic images IM1 of the subject. The first volume data V1 includes first contour data 51 representing the exterior of the subject and internal data 6 including the inside of the subject. In the conversion step, the first volume data V1 is converted to the second volume data V2 based on the reference contour data 50 other than the first contour data 51. The second volume data V2 includes a second contour data 52 different from the first contour data 51 and internal data 6 including the inside of the body of the subject.

According to such a mode, the anonymity of medical images can be ensured. In addition to guaranteeing anonymity, it also makes it possible to maintain the accuracy of machine learning. Since the second serial tomographic image IM2 provided as teacher data is only the contour data 5 replaced with the second contour data 52 from the first contour data 51, it is possible to maintain the accuracy of machine learning without damaging the internal data 6, which is important as teacher data.

3.2 Details of Information Processing

Here, a detailed portion of the information processing outlined in FIG. 4, is illustrated.

Figure 5:
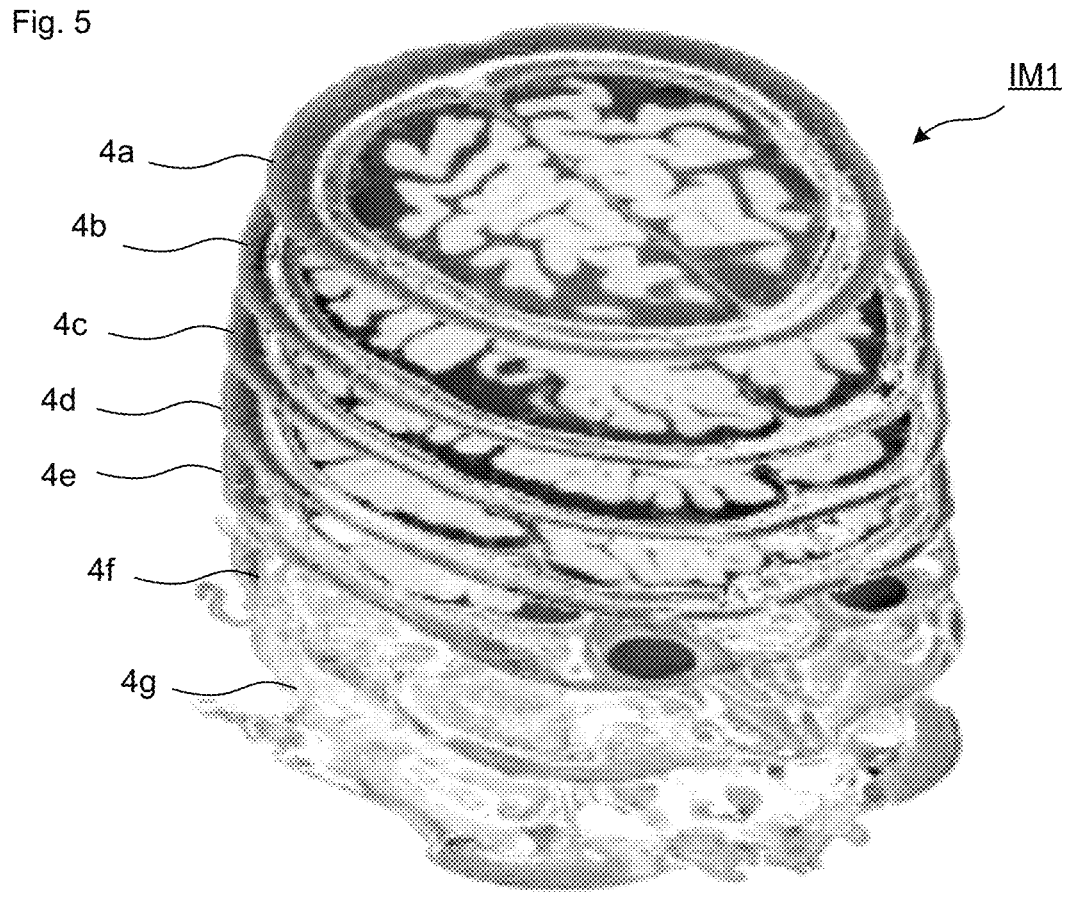
FIG. 5 is an overview diagram indicating an example of a first serial tomographic image IM1 (serial tomographic image IM).

FIG. 5 is an overview diagram indicating an example of a first serial tomographic image IM1 (serial tomographic image IM). As shown in FIG. 5, the serial tomographic image IM comprises a plurality of images. That is, the first serial tomographic image IM1 comprises a plurality of first images 4. The first images 4a, 4b, 4c, 4d, 4e, 4f and 4g are illustrated here, each of which is an image taken at each predetermined slice thickness. The slice thickness is not particularly limited, and is, for example, 0.1 to 20 mm, preferably 0.4 to 10 mm, more preferably 1 to 5 mm. Specifically, The slice thickness is, for example, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4, 5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20 mm, and may be within a range between any two values as described above. In particular, when the slice thickness value is small, the accuracy of face identification from the volume data V having been reconstructed will be higher, and the risk of the data falling under personal information will be increased.

Figure 6:
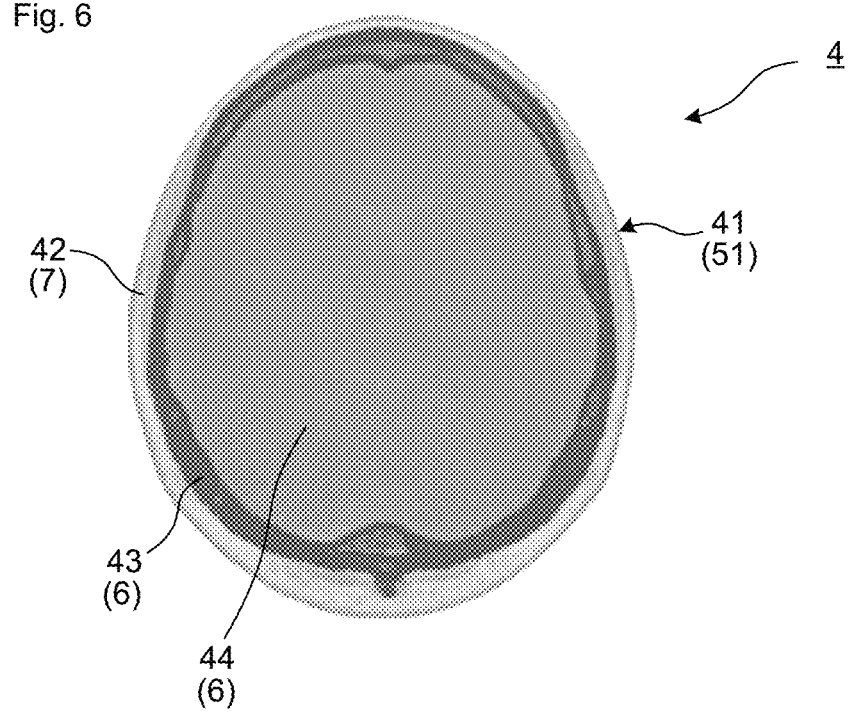
FIG. 6 is a schematic diagram indicating a first image 4, one of the first serial tomographic images IM1.

FIG. 6 is a schematic diagram indicating a first image 4, one of the first serial tomographic images IM1. As shown in FIG. 6, the first image 4 includes a body surface 41, an intermediate tissue 42, a bone 43, and a region 44 medial to bone 43. The body surface 41 is the element that determines the exterior of the first serial tomographic image IM1 when reconstructed into the first volume data V1, and the body surface 41 constitutes the first contour data 51. Pathologically, the body surface 41 includes at least the epidermis and the dermis. The intermediate tissue 42 includes at least one of subcutaneous tissue, muscle, fat and blood vessels, and constitutes intermediate data 7. The bone 43 and the region 44 medial to bone 43 comprise internal data 6, which may include cases.

In other words, the first contour data 51 represents the body surface 41 of the subject, and the internal data 6 represents the bone 43 and the region 44 medial to the bone 43, of the subject. The intermediate data 7 includes at least one of subcutaneous tissue, muscle, fat, and blood vessels intermediate tissue 42. In one embodiment, the intermediate tissue 42 is excluded as a location to identify cases, which means that such regions may be stretched or contracted. Such stretching is discussed in detail later using FIGS. 11A-11C. In this way, the integrity of the human body can be ensured and anonymity can also be ensured.

Figure 7:
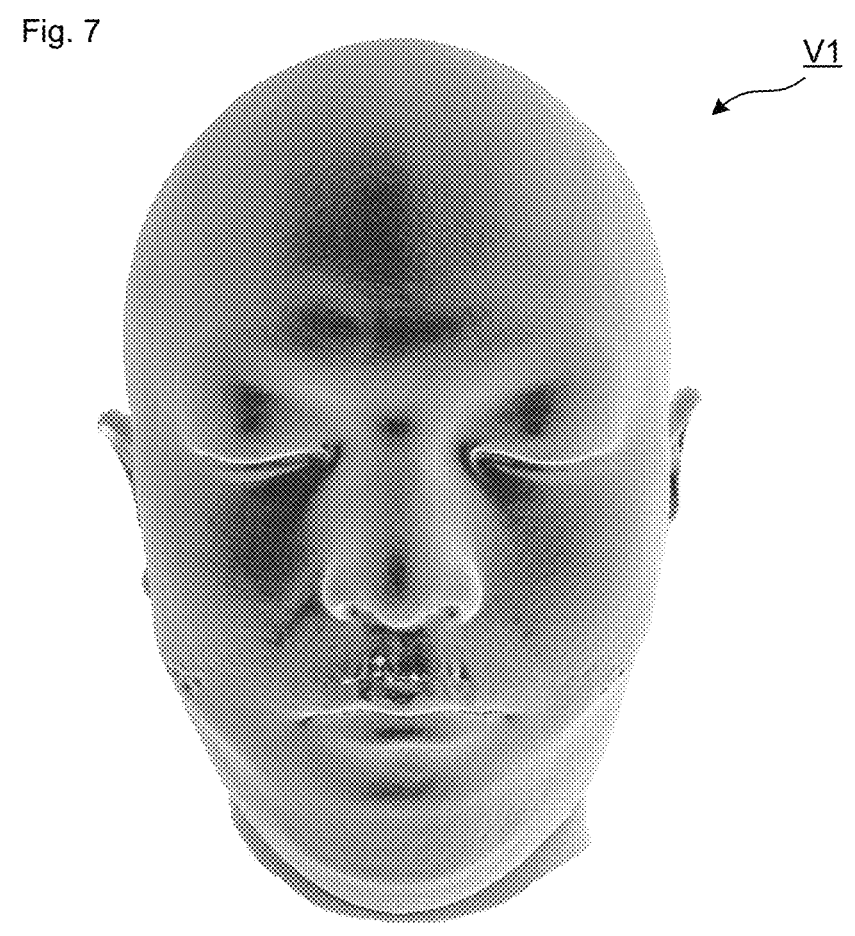
FIG. 7 is a schematic diagram indicating an example of first volume data V1 in which the face of the subject can be recognized.

FIG. 7 is a schematic diagram indicating an example of first volume data V1 in which the face of the subject can be recognized. As mentioned above, the first volume data V1 is obtained by reconstructing the first serial tomographic image IM1. The first volume data V1 reconstructed from the first serial tomographic image IM1 includes a first contour data 51 representing the exterior of the subject and an internal data 6 including the inside of the subject. Since the first volume data V1 includes the first contour data 51, the face (exterior) of the subject can be recognized, the first volume data V1 and the first serial tomographic image IM1 that is the source of the first volume data V1 can be subject to personal data protection.

Figure 8:
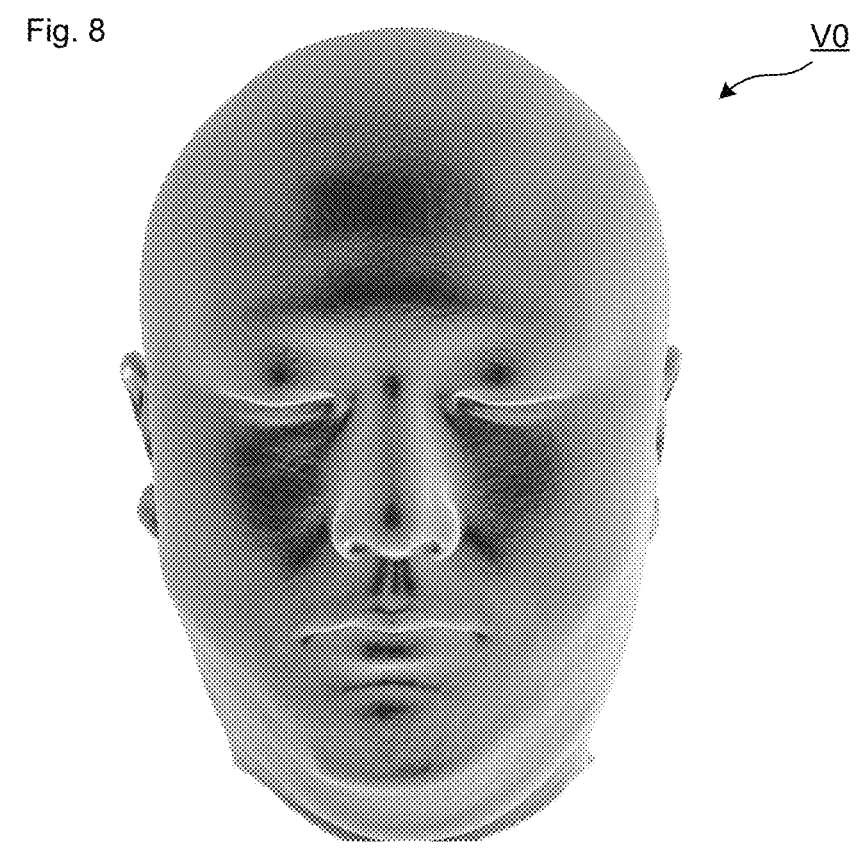
FIG. 8 is a schematic diagram indicating an example of reference volume data V0 that forms the face of a fictitious person.

FIG. 8 is a schematic diagram indicating an example of reference volume data V0 that forms the face of a fictitious person. As shown in FIGS. 7 and 8, the face recognized from the reference volume data V0 is different from that recognized from the first volume data V1. For example, the reference contour data 50 is calculated by the contour data of a person different from the subject. Thus, the reference contour data 50 can be easily generated because the contour data of a person different from the subject can be diverted from those that have been imaged in the past. Preferably, the reference contour data 50 is calculated by averaging a plurality of person images. Specifically, the reference contour data 50 should be calculated as an average value of the faces reconstructed from a plurality of medical images of the subject taken in the past. According to such a mode, the reference contour data 50, which is the contour data 5 of a fictitious person, can be generated by a simple algorithm of average calculation.

Here, preferably, the reference contour data 50 should be determined for at least one of age, gender or race. Since facial characteristics differ greatly depending on age, gender and race, it is recommended that a face that is an average of several, or reference contour data 50, be generated in advance, taking these conditions into account. According to such a mode, the reference contour data 50 that are close or identical to the attributes of the subject, especially age, gender and race, can be selected, which contributes to generating the second volume data V2 and the second serial tomographic image IM2 more naturally.

Even more preferably, the reference contour data 50 may be the second contour data 52 directly. In such a case, the reference volume data V0 itself, including the reference contour data 50, may be a deformed version of the first volume data V1. More specifically, the second contour data 52 may be obtained by deforming at least a part of the first contour data 51 based on preset reference information, for example, a learned model by GAN. GAN is a kind of generative model, by learning features from various data without correct data, which can generate data that does not exist or transform the data according to the features of the existing data. Thus, if the reference contour data 50 is originally obtained by deforming the first contour data 51, it can be more easily converted to the second volume data V2 including the second contour data 52 without reducing the processing by the registration unit 234 and setting unit 235, described above.

Figure 9B:
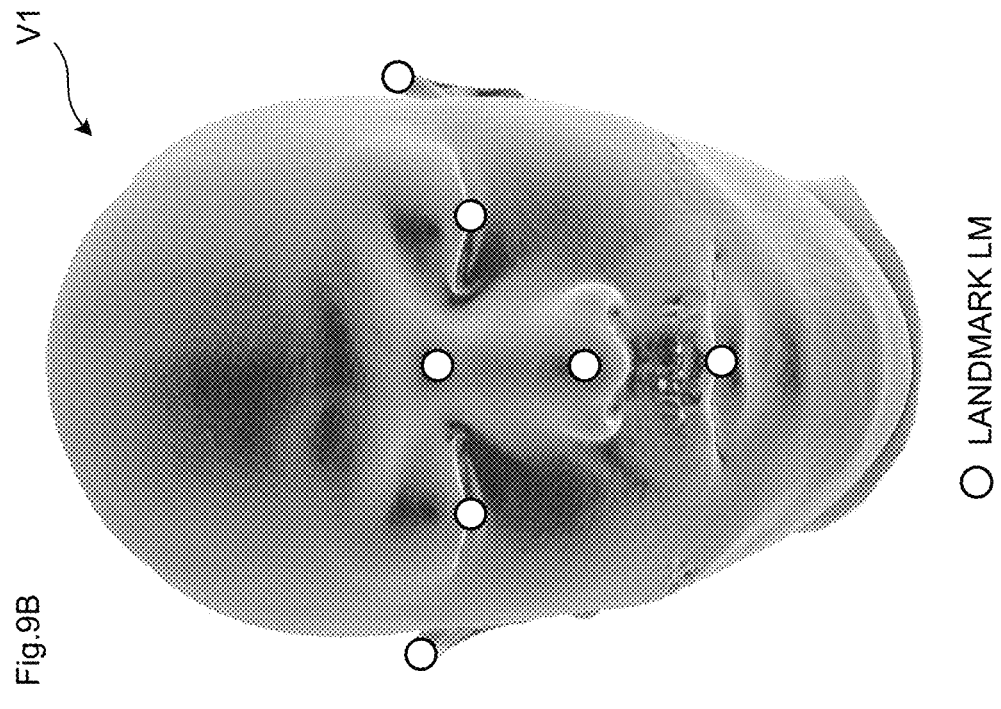
FIGS. 9A and 9B are schematic diagrams indicating the setting of landmark LM for volume data V.
Figure 9A:
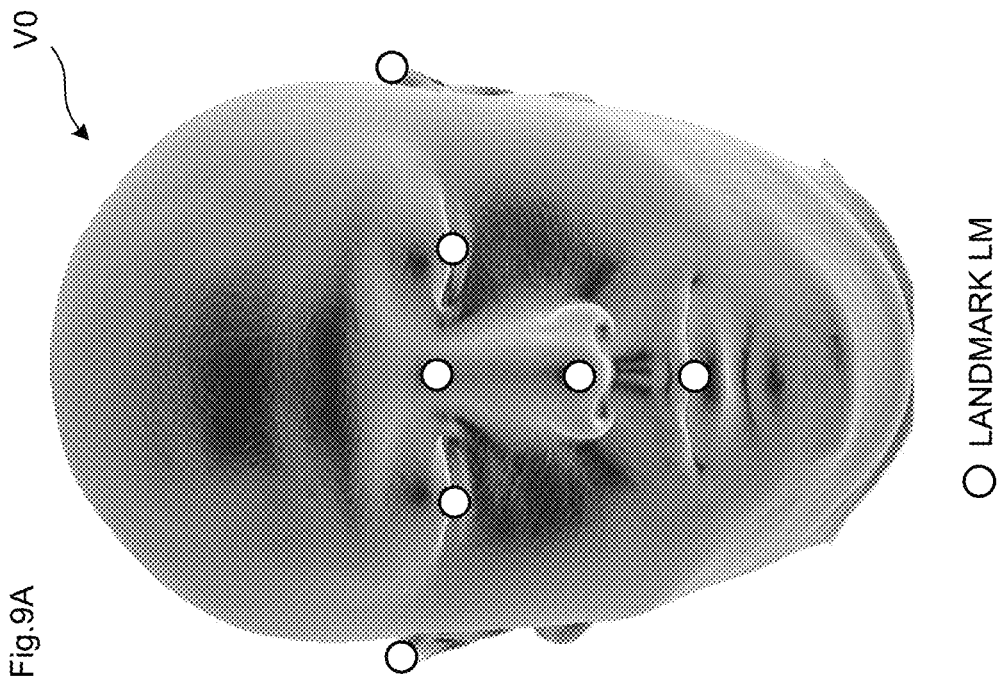

FIGS. 9A and 9B are schematic diagrams indicating the setting of landmark LM for volume data V. In the example shown in FIGS. 9A and 9B, landmarks LM are set at the center of the eyes, center of the mouth, between the eyebrows, vertex of the nose and vertex of the ears of the reference volume data V0 (FIG. 9A) and first volume data V1 (FIG. 9B), respectively. The center of the eyes, the center of the mouth, between the eyebrows, the apex of the nose and the apex of the ears are set respectively. For example, it may be implemented so that the reception unit 231 receives input using the input unit 25 of the subject and the setting unit 235 sets the landmarks LM based on the input. Alternatively, the controller 23 may be implemented to automatically detect at least one of the center of the eyes, the center of the mouth, between the eyebrows, the apex of the nose, and the apex of the ears by reading out a program with an automatic detection function stored in the storage unit 22. In addition, a combination of the functions thereof may be implemented to allow manual adjustment by input from the subject after automatic detection of the recommended locations for setting the landmark LM.

Figure 10:
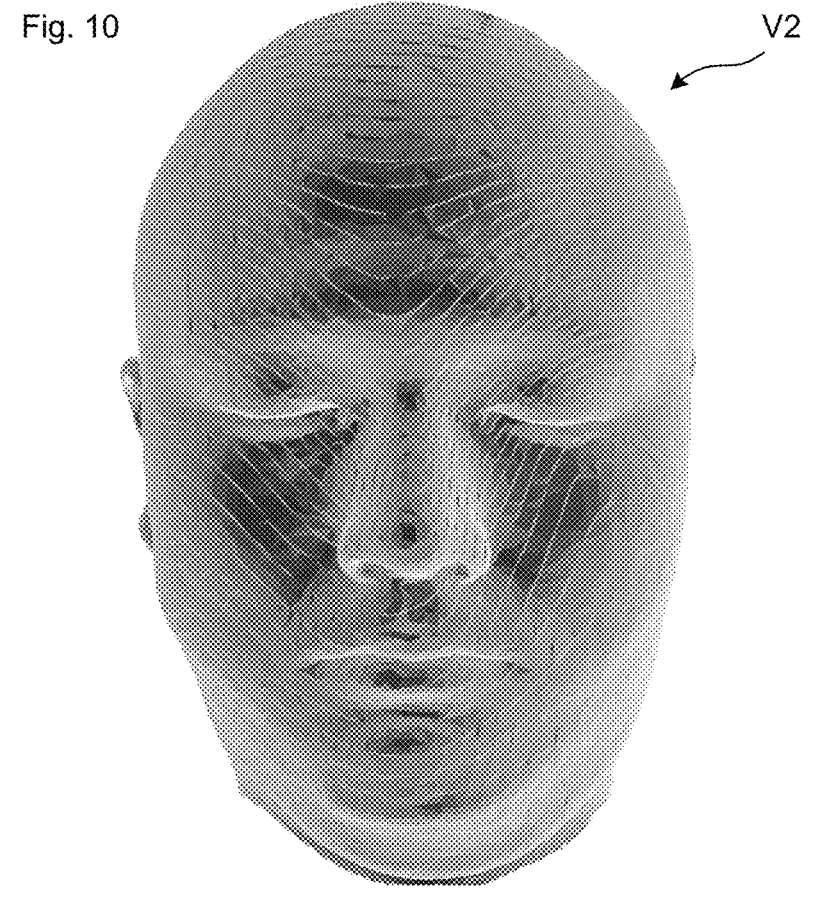
FIG. 10 is a schematic diagram indicating an example of second volume data V2 generated by the conversion.

FIG. 10 is a schematic diagram indicating an example of second volume data V2 generated by the conversion. As shown in FIG. 7 to FIG. 10, the face of the person formed in the second volume data V2 is different from both the face of the fictional person formed in the reference volume data V0 and the face of the subject formed in the first volume data V1. More specifically, after setting landmarks LM in the reference contour data 50 included in the reference volume data V0 and the first contour data 51 included in the first volume data V1, by referring the landmarks LM as a guide, The second volume data V2 with the second contour data 52 is obtained. Preferably, the thin spline method can be used to deform the reference volume data V0 so that the second volume data V2 is obtained. As mentioned above, the internal data 6 is not deformed before and after the conversion, only the contour data is deformed from the first contour data 51 to the second contour data 52.

In other words, the conversion unit 236 converts the first volume data V1 to the second volume data V2 with the second contour data 52 based on the landmark LM as a conversion step. By converting after setting the landmark LM, only the exterior of the subject can be changed more naturally, and further, the consistency of the subject as a human body can be ensured and anonymity can be ensured. In other words, the internal data 6 in the second volume data V2 is identical to the intermediate data 7 of the subject in the first volume data V1. In other words, the second volume data V2 comprises a second contour data 52 different from the first contour data 51 and the internal data 6 including the body of the subject.

Figure 11C:
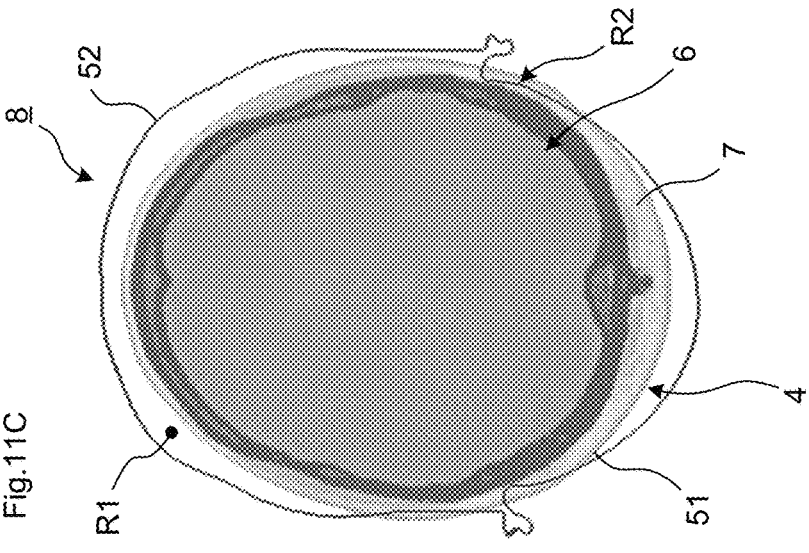
FIGS. 11A-11C are schematic diagrams indicating a second image 8, which is one of the second serial tomographic images IM2 generated from the second volume data V2.
Figure 11B:
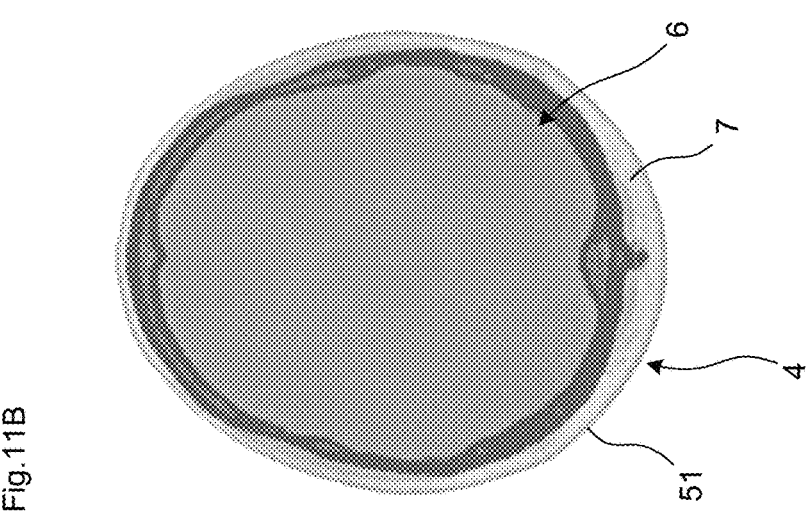
Figure 11A:
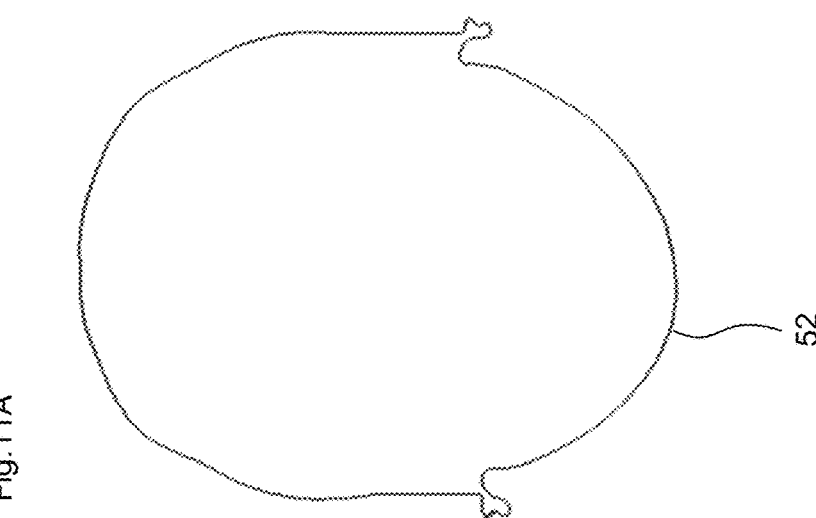

FIGS. 11A-11C are schematic diagrams indicating the second image 8, which is one of the second serial tomographic images IM2 generated from the second volume data V2. More particularly, from left to right, the second contour data 52 (FIG. 11A), the first image 4 (FIG. 11B), and the second image 8 (FIG. 11C) which is a combination of the second contour data 52 and the first image 4, is indicated. The second image 8 generated by the imaging unit 237 includes, in exterior, the second contour data 52 which can be reconstructed to obtain the second volume data V2 shown in FIG. 10. However, as shown in FIG. 11C, with only the contour data 5 being replaced, a blank region R1 or overflowing region R2 is included in the data.

Therefore, preferably, the correction unit 238 can execute a correction to stretch or shrink the intermediate data 7 to fit the second contour data 52 as a correction step. FIGS. 12A and 12B are schematic diagrams indicating the correction by deforming the internal data 6. Before correction (FIG. 12A), a blank region R1 exists between the first contour data 51 and the second contour data 52. Therefore, by stretching the intermediate data 7, subcutaneous 71 and muscle 72, by image processing to make them subcutaneous 71' and muscle 72', in other words, by making the first contour data 51 to be in line with the second contour data 52', the blank region R1 between the first contour data 51 and the second contour data 52 is not included in the data. Although not shown, to remove the overhang region R2, it is preferable to shrink the intermediate data 7, subcutaneous 71 and muscle 72, by image processing in the same way. According to this manner, not only can the exterior be changed by replacing the contour data 5, but also the integrity of the human body can be ensured, as well as anonymity.

[Others]

With respect to the information processing system 1 for one embodiment described above, the following may be adopted.

The first serial tomographic image IM1 provided by the hospital 12 may be implemented so that it is transmitted to the information processing apparatus 2 via the network 11.

In one embodiment, the reception unit 231, read-out unit 232, reconstruction unit 233, registration unit 234, setting unit 235, conversion unit 236, imaging unit 237, correction unit 238 and transmission unit 239 are described as functional units realized by controller 23 of information processing apparatus 2. However, at least some of them may be implemented as functional units realized by an unshown server, which is an example of an external device. In other words, a service for anonymizing the first serial tomographic image IM1 may be provided via the network 11.

Instead of the information processing apparatus 2, the first serial tomographic image IM1 may be stored directly on a server owned by the hospital 12, and the second serial tomographic image IM2 may be generated by performing the aforementioned process on the same. In such a case, it is preferable to obtain consent beforehand to provide the second serial tomographic image IM2 as machine learning teacher data at the time the subject is imaged. Further, the first volume data V1 reconstructing the first serial tomographic image IM1 may be provided by the hospital 12.

In one embodiment, the correction unit 238 corrects the second serial tomographic image IM2. However, it may be implemented so that the correction unit 238 executes correction on the second volume data V2 before the imaging unit 237 images the second volume data V2.

Depending on the reference volume data V0, the first volume data V1 and the second volume data V2 may be similar. To prevent such a situation, the controller 23 may read out the face recognition program stored in the storage unit 22 in advance and check each time whether the faces of the persons identified by the reference volume data V0 and the first volume data V1 are recognized as the same person.

The reference contour data 50 may be other than the contour data of a person different from the subject. For example, it may be the contour data of a fictitious person, or it may be the pre-processed contour data of the subject.

It may be implemented so that the second serial tomographic image IM2 may be managed in an unshown server instead of distributed ledger management by blockchain BC. It may also be implemented so that the second volume data V2 is shared instead of the second serial tomographic image IM2.

One embodiment may be implemented as a distributable program. This program is configured to allow a computer to execute each step in the information processing system 1.

In addition, it may be provided in each of the following forms (1) An information processing system, comprising a processor configured to execute a program so as to: in a reconstruction step, reconstruct a first volume data indicating at least a part of the subject based on a plurality of first serial tomographic images of the subject, wherein the first volume data includes first contour data representing an exterior of the subject and internal data including the inside of the subject; and in a conversion step, convert the first volume data to second volume data based on reference contour data other than the first contour data, wherein the second volume data includes a second contour data different from the first contour data and the internal data including the inside of the body of the subject including the first contour data and the internal data including the inside of the body of the subject.

(2) The information processing system according to (1), wherein the processor is further configured to execute the program so as to: in an imaging step, generate a plurality of second serial tomographic images from the second volume data.

(3) The information processing system according to (2), wherein the processor is further configured to execute the program so as to: in a reception step, receive the first serial tomographic images; and in a transmission step, transmit at least a part of the second serial tomographic images to an external device.

(4) The information processing system according to any one of (1) to (3), wherein: the volume data includes intermediate data indicating a region between the contour data and the internal data, and the processor is further configured to execute the program so as to, in a correction step, execute the correction to stretch or shrink the intermediate data to fit the second contour data.

(5) The information processing system according to (4), wherein: the intermediate data includes intermediate tissues including at least one of subcutaneous tissue, muscle, fat and blood vessels.

(6) The information processing system according to any one of (1) to (5), wherein: the reference contour data is calculated by at least one of contour data of a person different from the subject, contour data of a fictitious person, or pre-processed contour data of the subject.

(7) The information processing system according to (6), wherein: the reference contour data is calculated by averaging the contour data of a plurality of persons.

(8) The information processing system according to any one of (1) to (7), wherein: the reference contour data is determined by at least one of age, gender or race.

(9) The information processing system according to any one of (1) to (8), wherein the processor is further configured to execute the program so as to: in a registration step, register the first volume data and a reference volume data with the reference contour data; in a setting step, set a landmark for the first volume data and the reference volume data registered with each other; and in the conversion step, convert the first volume data to the second volume data with the second contour data based on the landmark.

(10) The information processing system according to any one of (1) to (9), wherein: the reference contour data is the second contour data; and the second contour data is obtained by deforming at least a part of the first contour data based on preset reference information.

(11) The information processing system according to any one of (1) to (10), wherein: the first contour data is data representing a body surface of the subject; and the internal data is data representing a bone and a region medial to the bone of the subject.

(12) Information processing method, comprising each step in the information processing system according to any one of claims 1 to 11.

(13) A program, configured to allow a computer to execute each step in the information processing system according to any one of claims 1 to 11.

The present invention is not limited to those.

Finally, various embodiments of the present invention have been described, but these are presented as examples and are not intended to limit the scope of the invention. The novel embodiment can be implemented in various other forms, and various omissions, replacements, and changes can be made without departing from the abstract of the invention. The embodiment and its modifications are included in the scope and abstract of the invention and are included in the scope of the invention described in the claims and the equivalent scope thereof.

What is claimed is:

1. An information processing system, comprising a processor configured to execute a program so as to:

in a reconstruction step, reconstruct a first volume data indicating at least a part of the subject based on a plurality of first serial tomographic images of the subject, wherein the first volume data includes first contour data representing an exterior of the subject and internal data including the inside of the subject; and in a conversion step, convert the first volume data to second volume data based on reference contour data other than the first contour data, wherein the second volume data includes a second contour data different from the first contour data and the internal data including the inside of the body of the subject including the first contour data and the internal data including the inside of the body of the subject.

2. The information processing system according to claim 1, wherein the processor is further configured to execute the program so as to:

in an imaging step, generate a plurality of second serial tomographic images from the second volume data.

3. The information processing system according to claim 2, wherein the processor is further configured to execute the program so as to:

in a reception step, receive the first serial tomographic images; and in a transmission step, transmit at least a part of the second serial tomographic images to an external device.

4. The information processing system according to claim 1, wherein:

the volume data includes intermediate data indicating a region between the contour data and the internal data, and the processor is further configured to execute the program so as to, in a correction step, execute the correction to stretch or shrink the intermediate data to fit the second contour data.

5. The information processing system according to claim 4, wherein:

the intermediate data includes intermediate tissues including at least one of subcutaneous tissue, muscle, fat and blood vessels.

6. The information processing system according to claim 1, wherein:

the reference contour data is calculated by at least one of contour data of a person different from the subject, contour data of a fictitious person, or pre-processed contour data of the subject.

7. The information processing system according to claim 6, wherein:

the reference contour data is calculated by averaging the contour data of a plurality of persons.

8. The information processing system according to claim 1, wherein:

the reference contour data is determined by at least one of age, gender or race.

9. The information processing system according to claim 1, wherein the processor is further configured to execute the program so as to:

in a registration step, register the first volume data and a reference volume data with the reference contour data;

in a setting step, set a landmark for the first volume data and the reference volume data registered with each other; and in the conversion step, convert the first volume data to the second volume data with the second contour data based on the landmark.

10. The information processing system according to claim 1, wherein:

the reference contour data is the second contour data; and the second contour data is obtained by deforming at least a part of the first contour data based on preset reference information.

11. The information processing system according to claim 1, wherein:

the first contour data is data representing a body surface of the subject; and the internal data is data representing a bone and a region medial to the bone of the subject.

12. An information processing method, comprising each step in the information processing system according to claim 1.

13. A non-transitory computer-readable memory medium storing a program, configured to allow a computer to execute each step in the information processing system according to claim 1.

* * * * *